(12) United States Patent
Oohara et al.

(10) Patent No.: US 7,411,096 B2
(45) Date of Patent: Aug. 12, 2008

(54) PROCESS FOR PRODUCING OPTICALLY ACTIVE PHOSPHORUS HETEROCYCLIC DIMER

(75) Inventors: Nobuhiko Oohara, Tokyo (JP); Tsuneo Imamoto, Chiba (JP)

(73) Assignee: Nippon Chemical Industrial Co., Ltd., Koto-ku (JP)

( * ) Notice: Subject to any disclaimer, the term of this patent is extended or adjusted under 35 U.S.C. 154(b) by 285 days.

(21) Appl. No.: 10/564,985

(22) PCT Filed: Jul. 27, 2004

(86) PCT No.: PCT/JP2004/010671

§ 371 (c)(1),
(2), (4) Date: Jan. 18, 2006

(87) PCT Pub. No.: WO2005/010014

PCT Pub. Date: Feb. 3, 2005

(65) Prior Publication Data

US 2006/0211888 A1  Sep. 21, 2006

(30) Foreign Application Priority Data

Jul. 28, 2003 (JP) ............................. 2003-280584

(51) Int. Cl.
C07F 9/50 (2006.01)
C07F 9/547 (2006.01)
(52) U.S. Cl. ...................................... 568/12
(58) Field of Classification Search .................... 568/12
See application file for complete search history.

(56) References Cited

U.S. PATENT DOCUMENTS 7,169,953 B2 * 1/2007 Zhang et al. .................... 568/8

FOREIGN PATENT DOCUMENTS

WO   WO 03/042135 A   5/2003

OTHER PUBLICATIONS

Ohashi et al. (Heterocycles 2000, 52(2), 905-910)—a printout of the CAS Abstract and reacation are attached.*
Burk, J. et al., "Preparation and Use of C$_2$-Symmetric Bis(phospholanes): Production of α-Amino Acid Derivatives via Highly Enantioselective Hydrogenation Reactions", J. Am. Chem. Soc., 1993, pp. 10125-10138, vol. 115, No. 22, American Chemical Society.
Imamoto, T. et al., "P-Chiral Bis(trialkylphosphine) Ligands and Their Use in Highly Enantioselective Hydrogenation Reactions", J. Am. Chem. Soc., 1998, pp. 1635-1636, vol. 120, No. 7, American Chemical Society.
Imamoto T. et al., "Optically Active 1,1'-Di-tert-butyl-2,2'-diphosphetanyl and Its Application in Rhodium-Catalyzed Asymmetric Hydrogenations", Synthesis 2004, 2004, pp. 1353-1358, No. 9, Georg Thieme Verlag Stuttgart, New York.

* cited by examiner

Primary Examiner—Rebecca L Anderson
Assistant Examiner—Jason M Nolan
(74) Attorney, Agent, or Firm—Smith Patent Office

(57) ABSTRACT

The present invention provides a process for producing an optically active phosphorus heterocyclic dimer including reacting, in the presence of a base, primary phosphine represented by formula (1)

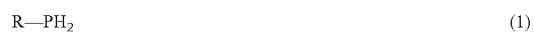

is reacted with a compound represented by formula (2)

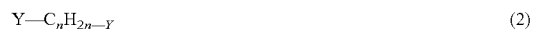

in the presence of a base; the product is reacted with boron trihydride, oxygen, or sulfur to obtain a phosphorus heterocyclic compound represented by formula (3):

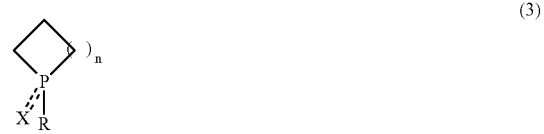

the resultant compound is dimerized to produce a phosphorus heterocyclic dimer represented by formula (4):

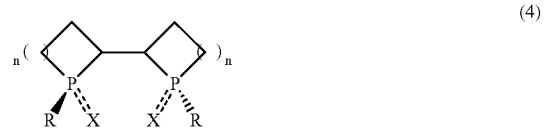

and then oxygen, sulfur, or borane is removed from the resultant phosphorus heterocyclic dimer to obtain an optically active phosphorus heterocyclic dimer represented by formula (5):

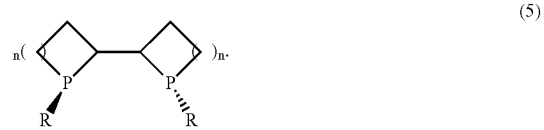

1 Claim, No Drawings

PROCESS FOR PRODUCING OPTICALLY ACTIVE PHOSPHORUS HETEROCYCLIC DIMER

TECHNICAL FIELD

The present invention relates to a process for producing an optically active phosphorus heterocyclic dimer.

BACKGROUND ART

Catalytic asymmetric synthesis reaction using an optically active catalyst (referred to as an "asymmetric catalyst" hereinafter) is capable of synthesizing a large amount of an optically active compound using a very small amount of an asymmetric catalyst, and is thus highly valued in industrial use. In particular, a synthesis method referred to as "asymmetric reduction" has the advantage of high reaction efficiency and the advantage that by-products such as an inorganic salt and the like are not produced in use of hydrogen gas as a raw material. Therefore, this synthesis method is economical and harmonizes with environments.

The catalytic asymmetric synthesis reaction is aimed at producing a product with high optical purity, the optical purity depending on the performance of the asymmetric catalyst used in the reaction. Although a transition metal complex is generally used as the asymmetric catalyst, the optical purity of a reaction product is mostly determined by the type of the asymmetric space created by the ligand coordinating to a transition metal of the complex at a reaction site. Therefore, in development of an asymmetric catalyst, it is most important to design the configuration of a ligand so as to realize excellent catalytic activity and stereoselectivity.

In recent years, asymmetric ligands have been actively studied, and various asymmetric ligands have been developed. In particular, phosphine ligands play an important role in catalytic asymmetric synthesis reaction using a transition metal complex. A huge amount of ligands has been designed and synthesized so far.

The inventors of the present invention proposed 1,2-bis(alkylmethylphosphino)ethane capable of efficiently asymmetrically hydrogenating various α,β-unsaturated α-amino acids and esters thereof, having a phosphorus-chiral trialkyl group, and represented by the following formula (9):

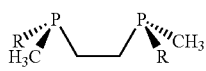
(9)

(wherein R represents cyclopentyl, cyclohexyl, tert-butyl, 1,1-diethylpropyl, or 1-adamantyl) (Non-patent Document 1).

Among ligands having phosphorus-containing heterocyclic rings, ligands having strong structures due to heterocyclic rings are known to suppress the number of conformations of a chelate formed by coordination to a central metal and create a stable asymmetric space (Non-patent Document 2).

An optically active phosphorus-chiral diphosphine represented by formula (9) has no heterocyclic ring, and it is thus difficult to say, depending on the substituent represented by R and bonded to each phosphorus atom, that the structure of the ligand is stable.

[Non-patent Document 1]
J. Am. Chem. Soc., 1998, 120, pp. 1635-1636
[Non-patent Document 2]
J. Am. Chem. Soc., 1993, 115, pp. 10125-10138

Accordingly, an object of the present invention is to provide a process for producing a novel optically active phosphorus heterocyclic dimer useful as a ligand of a transition metal catalyst which is used for catalytic asymmetric synthesis such as asymmetric hydrogenation reaction and the like, the ligand capable of creating a stable asymmetric space when coordinating to a central metal.

DISCLOSURE OF THE INVENTION

In the above-mentioned situation, the intensive research conducted by the inventors of the present invention resulted in the achievement of the present invention. In other words, the present invention provides a process for producing an optically active phosphorus heterocyclic dimer including reacting, in the presence of a base, primary phosphine represented by formula (1):

[Chem. 2]

$$R-PH_2 \tag{1}$$

(wherein R represents a linear, branched, or cyclic alkyl group having 2 to 20 carbon atoms) with a compound represented by formula (2):

[Chem. 3]

$$Y-C_nH_{2n}-Y \tag{2}$$

(wherein Y represents a halogen atom or a leaving group selected from -OTs, -OTf, and -OMs, and n represents a number of 3 to 6); reacting the product with boron trihydride, oxygen, or sulfur to obtain a phosphorus heterocyclic compound represented by formula (3):

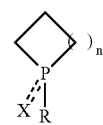
(3)

(wherein R represents the same as the above, n represents a number of 1 to 4, X represents a boron trihydride group, an oxygen atom, or a sulfur atom, and ══ represents a single bond when X is a boron trihydride group or a double bond when X is an oxygen atom or sulfur atom); dimerizing the resultant compound to produce a phosphorus heterocyclic dimer represented by formula (4):

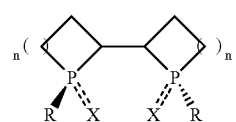
(4)

(wherein R, n, and X represent the same as the above); and then removing oxygen, sulfur, or borane from the resultant phosphorus heterocyclic dimer to obtain an optically active phosphorus heterocyclic dimer represented by formula (5):

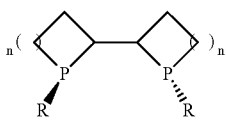

(wherein R and n represent the same as the above).

BEST MODE FOR CARRYING OUT THE INVENTION

A process for producing an optically active phosphorus heterocyclic dimer of the present invention is represented by Reaction Formula (1):

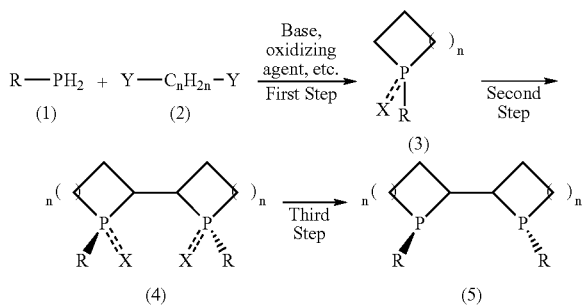

The production process of the present invention includes a first step of reacting primary phosphine represented by formula (1) with a compound represented by formula (2) in the presence of a base and then reacting the reaction product with boron trihydride, oxygen, or sulfur to obtain a phosphorus heterocyclic compound represented by formula (3); a second step of dimerizing the compound of formula (3) to obtain a phosphorus heterocyclic dimer represented by formula (4); and a third step of removing oxygen, sulfur, or borane from the phosphorus heterocyclic dimer represented by formula (4) to obtain an optically active phosphorus heterocyclic dimer represented by formula (5).

<First Step>

In the first step, primary phosphine (1) is reacted with a compound represented by formula (2) in the presence of a base and then reacted with boron trihydride, oxygen, or sulfur to obtain a phosphorus heterocyclic compound represented by formula (3).

The primary phosphine used as a raw material is represented by formula (1):

[Chem. 8]

R—PH$_2$ (1)

R is a linear, branched, or cyclic alkyl group having 2 to 20 carbon atoms. Examples of such an alkyl group include ethyl, isopropyl, n-propyl, isobutyl, n-butyl, sec-butyl, tert-butyl, isoheptyl, n-heptyl, isohexyl, n-hexyl, cyclopentyl, cyclohexyl, 1-methylcyclohexyl, and adamantyl. Usable examples of the primary phosphine include tert-butylphosphine, ethylphosphine, isopropylphosphine, n-propylphosphine, isbutylphosphine, n-butylphosphine, sec-butylphosphine, isoheptylphosphine, n-heptylphosphine, isohexylphosphine, n-hexylphosphine, cyclopentylphosphine, cyclohexylphosphine, and 1-methylcyclohexylphosphine. As the phosphine, commercially available phosphine may be used. Alternatively, phosphine synthesized by addition reaction of phosphine gas and an olefin or reduction of alkyldihalogenylphosphine, which is prepared from phosphorus halide and an alkyl Grignard reagent, with lithium aluminum hydride or the like may be used. The monoalkyl phosphine used preferably has a purity of 95% or more from the viewpoint of suppressing by-products.

Another raw material is a compound represented by formula (2):

[Chem. 9]

Y—C$_n$H$_{2n}$—Y (2)

In this formula, Y represents a halogen atom or a leaving group selected from -OTs, -OTf, and -OMs, and n represents a number of 3 to 6. Herein, -OTs represents tosyloxy, -OTf represents trifluoromethanesulfonyloxy, and -OMs represents methanesulfonyloxy.

Examples of the compound represented by formula (2) include 1,3-dichloropropane, 1,3-dibromopropane, 1,3-bis(tosyloxy)propane, 1,3-bis(mesyloxy)propane, 1,3-bis(trifluoroxy)propane, 1,4-dichlorobutane, 1,4-dibromobutane, 1,4-bis(tosyloxy)butane, 1,4-bis(mesyloxy)butane, 1,4-bis(trifluoroxy)butane, 1,5-dichloropentane, 1,5-dibromopentane, 1,5-bis(tosyloxy)pentane, 1,5-bis(mesyloxy)pentane, 1,5-bis(trifluoroxy)pentane, 1,6-dichlorohexane, 1,6-dibromohexane, 1,6-bis(tosyloxy)hexane, 1,6-bis(mesyloxy)hexane, and 1,6-bis(trifluoroxy)hexane. As the compound, a commercially available compound may be used, or the compound may be synthesized according to a known method, e.g., the method described in J. Am. Chem. Soc., 1993, 115, p. 10134. Among these compounds, 1,3-dichloropropane is most preferred because of easy availability, low cost, and relatively high product yield.

As the base, n-butyl lithium, sec-butyl lithium, and the like may be used, or a commercially available base may be used. From the viewpoint that an appropriate amount can be added, and side reaction can be prevented, preferably, the concentration of the base is precisely determined by titration in advance.

When X in the phosphorus heterocyclic compound represented by formula (3) and produced by the first step is a borane complex, a borane-THF complex, a borane-dimethyl sulfide complex, or the like can be used. When X is an oxygen atom, an oxidizing agent such as hydrogen peroxide or the like can be used. When X is a sulfur atom, a sulfurizing agent such as sulfur powder or the like can be used.

In the first step, first, the primary phosphine (1) is reacted with the compound represented by formula (2) in the presence of the base.

The solvent used is not particularly limited as long as it does not react with a reaction agent and the like. However, diethyl ether, tetrahydrofuran (referred to as "THF" hereinafter), n-hexane, toluene, and the like can be used alone or as a mixture of two or more. The solvent is preferably dehydrated by an ordinary method before use.

The reaction conditions and temperature depend on the electrophilic reagent used. For example, when 1,3-dichloropropane is used, it is necessary that a solution of the primary phosphine and 1,3-dichloropropane is cooled to −78 to −50° C. and preferably −70 to −78° C., and n-butyl lithium is slowly added dropwise. The inside of the reactor used is preferably sufficiently dried and replaced with inert gas from the viewpoint of prevention of moisture deactivation of the base and oxygen oxidation of the phosphine. Then, the reaction solution is heated to −20 to 0° C., and any one of a borane complex, an oxidizing agent, and a sulfurizing agent is added to the reaction solution. After reaction for 0.5 to 2 hours, pure water is added to the reaction solution to terminate the reaction. An aqueous layer is separated from the resultant mixture of an organic layer and the aqueous layer, and the organic layer is washed with pure water and then an aqueous inorganic salt solution, and dehydrated. After, the organic solvent is removed, the residue is dried to obtain a crude phosphorus heterocyclic compound. The resulting crude phosphorus heterocyclic compound can be purified by an ordinary method such as recrystallization, column chromatography, distillation, or the like. As a result, the phosphorus heterocyclic compound represented by formula (3) can be obtained.

Examples of the compound represented by formula (3) include four-membered ring compounds, such as 1-tert-butyl-phosphetane 1-sulfide, 1-ethyl-phosphetane 1-sulfide, 1-isopropyl-phosphetane 1-sulfide, 1-n-propyl-phosphetane 1-sulfide, 1-isbutyl-phosphetane 1-sulfide, 1-n-butyl-phosphetane 1-sulfide, 1-isoheptyl-phosphetane 1-sulfide, 1-n-heptyl-phosphetane 1-sulfide, 1-isohexyl-phosphetane 1-sulfide, 1-n-hexyl-phosphetane 1-sulfide, 1-cyclopentyl-phosphetane 1-sulfide, 1-cyclohexyl-phosphetane 1-sulfide, 1-1-methylcyclohexyl-phosphetane 1-sulfide, 1-adamantyl-phosphetane 1-sulfide, 1-tert-butyl-phosphetane 1-oxide, 1-ethyl-phosphetane 1-oxide, 1-isopropyl-phosphetane 1-oxide, 1-n-propyl-phosphetane 1-oxide, 1-isobutyl phosphetane 1-oxide, 1-n-butyl-phosphetane 1-oxide, 1-isoheptyl-phosphetane 1-oxide, 1-n-heptyl-phosphetane 1-oxide, 1-isohexyl-phosphetane 1-oxide, 1-n-hexyl-phosphetane 1-oxide, 1-cyclopentyl-phosphetane 1-oxide, 1-cyclohexyl-phosphetane 1-oxide, 1-1-methylcyclohexyl-phosphetane 1-oxide, 1-adamantyl-phosphetane 1-oxide, 1-boranato-1-t-butyl phosphetane, 1-boranato-1-ethyl-phosphetane, 1-boranato-1-isopropyl-phosphetane, 1-boranato-1-n-propyl-phosphetane, 1-boranato-1-isobutyl-phosphetane, 1-boranato-1-n-butyl-phosphetane, 1-boranato-1-sec-butyl-phosphetane, 1-boranato-1-isoheptyl-phosphetane, 1-boranato-1-n-heptyl-phosphetane, 1-boranato-1-isohexyl-phosphetane, 1-boranato-1-n-hexyl-phosphetane, 1-boranato-1-cyclopentyl-phosphetane, 1-boranato-1-cyclohexyl-phosphetane, 1-boranato-1-1-methylcyclohexyl-phosphetane, and 1-boranato-1-adamantyl-phosphetane.

Examples of the compound represented by formula (3) also include five-membered ring compounds, such as 1-tert-butyl-phosphorane 1-sulfide, 1-ethyl-phosphorane 1-sulfide, 1-isopropyl-phosphorane 1-sulfide, 1-n-propyl-phosphorane 1-sulfide, 1-isobutyl-phosphorane 1-sulfide, 1-n-butyl-phosphorane 1-sulfide, 1-isoheptyl-phosphorane 1-sulfide, 1-n-heptyl-phosphorane 1-sulfide, 1-isohexyl-phosphorane 1-sulfide, 1-n-hexyl-phosphorane 1-sulfide, 1-cyclopentyl-phosphorane 1-sulfide, 1-cyclohexyl-phosphorane 1-sulfide, 1-1-methylcyclohexyl-phosphorane 1-sulfide. 1-adamantyl-phosphorane 1-sulfide, 1-tert-butyl-phosphorane 1-oxide, 1-ethyl-phosphorane 1-oxide, 1-isopropyl-phosphorane 1-oxide, 1-n-propyl-phosphorane 1-oxide, 1-isobutyl-phosphorane 1-oxide, 1-n-butyl-phosphorane 1-oxide, 1-isoheptyl-phosphorane 1-oxide, 1-n-heptyl-phosphorane 1-oxide, 1-isohexyl-phosphorane 1-oxide, 1-n-hexyl-phosphorane 1-oxide, 1-cyclopentyl-phosphorane 1-oxide, 1-cyclohexyl-phosphorane 1-oxide, 1-1-methylcyclohexyl-phosphorane 1-oxide, 1-adamantyl-phosphorane 1-oxide, 1-boranato-1-tert-butyl-phosphorane, 1-boranato-1-ethyl-phosphorane, 1-boranato-1-isopropyl-phosphorane, 1-boranato-1-n-propyl-phosphorane, 1-boranato-1-isobutyl-phosphorane, 1-boranato-1-n-butyl-phosphorane, 1-boranato-1-sec-butyl-phosphorane, 1-boranato-1-isoheptyl-phosphorane, 1-boranato-1-n-heptyl-phosphorane, 1-boranato-1-isohexyl-phosphorane, 1-boranato-1-n-hexyl-phosphorane, 1-boranato-1-cyclopentyl-phosphorane, 1-boranato-1-cyclohexyl-phosphorane, 1-boranato-1-1-methylcyclohexyl-phosphorane, and 1-boranato-1-adamantyl-phosphorane.

Examples of the compound represented by formula (3) further include six-membered ring compounds, such as 1-tert-butyl-phosphinane 1-sulfide, 1-ethyl-phosphinane 1-sulfide, 1-isopropyl-phosphinane 1-sulfide, 1-n-propyl-phosphinane 1-sulfide, 1-isobutyl-phosphinane 1-sulfide, 1-n-butyl-phosphinane 1-sulfide, 1-isoheptyl-phosphinane 1-sulfide, 1-n-heptyl-phosphinane 1-sulfide, 1-isohexyl-phosphinane 1-sulfide, 1-n-hexyl-phosphinane 1-sulfide, 1-cyclopentyl-phosphinane 1-sulfide, 1-cyclohexyl-phosphinane 1-sulfide, 1-1-methylcyclohexyl-phosphinane 1-sulfide, 1-adamantyl-phosphinane 1-sulfide, 1-tert-butyl-phosphinane 1-oxide, 1-ethyl-phosphinane 1-oxide, 1-isopropyl-phosphinane 1-oxide, 1-n-propyl-phosphinane 1-oxide, 1-isobutyl-phosphinane 1-oxide, 1-n-butyl-phosphinane 1-oxide, 1-isoheptyl-phosphinane 1-oxide, 1-n-heptyl-phosphinane 1-oxide, 1-isohexyl-phosphinane 1-oxide, 1-n-hexyl-phosphinane 1-oxide, 1-cyclopentyl-phosphinane 1-oxide, 1-cyclohexyl-phosphinane 1-oxide, 1-1-methylcyclohexyl-phosphinane 1-oxide, 1-adamantyl-phosphinane 1-oxide, 1-boranato-1-tert-butyl-phosphinane, 1-boranato-1-ethyl-phosphinane, 1-boranato-1-isopropyl-phosphinane, 1-boranato-1-n-propyl-phosphinane, 1-boranato-1-isobutyl-phosphinane, 1-boranato-1-n-butyl-phosphinane, 1-boranato-1-sec-butyl-phosphinane, 1-boranato-1-isoheptyl-phosphinane, 1-boranato-1-n-heptyl-phosphinane, 1-boranato-1-isohexyl-phosphinane, 1-boranato-1-n-hexyl-phosphinane, 1-boranato-1-cyclopentyl-phosphinane, 1-boranato-1-cyclohexyl-phosphinane, 1-boranato-1-1-methylcyclohexyl-phosphinane, and 1-boranato-1-adamantyl-phosphinane.

Examples of the compound represented by formula (3) further include seven-membered ring compounds, such as 1-tert-butyl-phosphepane 1-sulfide, 1-ethyl-phosphepane 1-sulfide, 1-isopropyl-phosphepane 1-sulfide, 1-n-propyl-phosphepane 1-sulfide, 1-isobutyl-phosphepane 1-sulfide, 1-n-butyl-phosphepane 1-sulfide, 1-isoheptyl-phosphepane 1-sulfide, 1-n-heptyl-phosphepane 1-sulfide, 1-isohexyl-phosphepane 1-sulfide, 1-n-hexyl-phosphepane 1-sulfide, 1-cyclopentyl-phosphepane 1-sulfide, 1-cyclohexyl-phosphepane 1-sulfide, 1-1-methylcyclohexyl-phosphepane 1-sulfide, 1-adamantyl-phosphepane 1-sulfide, 1-tert-butyl-phosphepane 1-oxide, 1-ethyl-phosphepane 1-oxide, 1-isopropyl-phosphepane 1-oxide, 1-n-propyl-phosphepane 1-oxide, 1-isobutyl-phosphepane 1-oxide, 1-n-butyl-phosphepane 1-oxide, 1-isoheptyl-phosphepane 1-oxide, 1-n-heptyl-phosphepane 1-oxide, 1-isohexyl-phosphepane 1-oxide, 1-n-hexyl-phosphepane 1-oxide, 1-cyclopentyl-phosphepane 1-oxide, 1-cyclohexyl-phosphepane 1-oxide, 1-1-methylcyclohexyl-phosphepane 1-oxide, 1-adamantyl-phosphepane 1-oxide, 1-boranato-1-tert-butyl-phosphepane, 1-boranato-1-ethyl-phosphepane, 1-boranato-1-isopropyl-phosphepane, 1-boranato-1-n-propyl-phosphepane, 1-boranato-1-isobutyl-phosphepane, 1-boranato-1-n-butyl-phosphepane, 1-boranato-1-sec-butyl-phosphepane, 1-boranato-1-isoheptyl-phosphepane, 1-boranato-1-n-heptyl-phosphepane, 1-boranato-1-isohexyl-phosphepane, 1-boranato-1-n-hexyl-phosphepane, 1-boranato-1-cyclopentyl-phosphepane, 1-boranato-1-cyclohexyl-phosphepane, 1-boranato-1-1-methylcyclohexyl-phosphepane, and 1-boranato-1-adamantyl-phosphepane.

<Second Step>

In the second step, the phosphorus heterocyclic compound represented by formula (3) is dimerized.

First, (−)-sparteine and a solvent are added to a reactor and cooled to −50° C. or less, and a n-butyl lithium or sec-butyl lithium solution is added to the reactor. The resultant mixture is stirred to prepare a butyl lithium/(−)-sparteine complex.

As the (−)-sparteine, a commercially available reagent is preferably distilled and then used.

As the n-butyl lithium or sec-butyl lithium, a commercially available compound can be used. From the viewpoint that an appropriate amount can be added, and side reaction can be prevented, the concentration of the n-butyl lithium or sec-butyl lithium is preferably precisely determined by titration in advance.

The reaction temperature is −50° C. or less and preferably −70° C. or less. The butyl lithium/(−)-sparteine complex is a reagent effective in stereoselective deprotonation reaction of a prochiral methyl group.

Next, a solution of the purified phosphorus heterocyclic compound in an organic solvent is added to a solution of the butyl lithium/(−)-sparteine complex, followed by reaction at −50 to −78° C. for 3 to 8 hours. Then, copper chloride is added to the reaction solution, and the reaction solution is gradually heated to room temperature under stirring over 2 to 3 hours, followed by further reaction at room temperature for 3 to 15 hours. The copper chloride used is preferably sufficiently ground by a mortar and dried in advance. The solvent used is not particularly limited as long as it is an aprotic organic solvent which does not inhibit coordination of (−)-sparteine to lithium and which does not solidify at low temperatures. As the solvent, a single solvent or a mixture of two or more solvents may be used, but diethyl ether is preferred from the viewpoint of the high formation rate of the butyl lithium/(−)-sparteine complex. The inside of the reactor is preferably sufficiently dried and replaced by inert gas before the reaction, and the reaction is preferably performed under an inert gas stream from the viewpoint that deactivation of the butyl lithium/(−)-sparteine complex can be prevented.

Thereafter, conc. ammonia water is added to the reaction solution to terminate the reaction. An organic layer is separated, and an aqueous layer is subjected to extraction with a polar solvent such as acetic acid. The organic layers are collected, washed, and dehydrated, and then the extraction solvent is removed to obtain a crude mixture of a phosphorus heterocyclic compound dimer represented by formula (4). Then, the mixture is purified by ordinary means such as silica gel column chromatography or the like and recrystallization to obtain an optically pure phosphorus heterocyclic compound dimer represented by formula (4). The optical purity of the compound represented by formula (4) can be measured by HPLC analysis using a commercial optically active column.

Examples of the phosphorus heterocyclic compound dimer represented by formula (4) include four-membered heterocyclic compounds, such as (1R,1R',2R,2R')-1,1'-di-tert-butyl-[2,2']-diphosphetanyl 1,1'-disulfide, (1R,1R',2R,2R')-1,1'-di-ethyl-[2,2']-diphosphetanyl 1,1'-disulfide, (1R,1R',2R,2R')-1,1'-di-isopropyl-[2,2']-diphosphetanyl 1,1'-disulfide, (1R,1R',2R,2R')-1,1'-di-n-propyl-[2,2']-diphosphetanyl 1,1'-disulfide, (1R,1R',2R,2R')-1,1'-di-isobutyl-[2,2']-diphosphetanyl 1,1'-disulfide, (1R,1R',2R,2R')-1,1'-di-n-butyl-[2,2']-diphosphetanyl 1,1'-disulfide, (1R,1R',2R,2R')-1,1'-di-isoheptyl-[2,2']-diphosphetanyl 1,1'-disulfide, (1R,1R',2R,2R')-1,1'-di-n-heptyl-[2,2']-diphosphetanyl 1,1'-disulfide, (1R,1R',2R,2R')-1,1'-di-isohexyl-[2,2']-diphosphetanyl 1,1'-disulfide, (1R,1R',2R,2R')-1,1'-di-n-hexyl-[2,2']-diphosphetanyl 1,1'-disulfide, (1R,1R',2R,2R')-1,1'-di-cyclopentyl-[2,2']-diphosphetanyl 1,1'-disulfide, (1R,1R',2R,2R')-1,1'-di-cyclohexyl-[2,2']-diphosphetanyl 1,1'-disulfide, (1R,1R',2R,2R')-1,1'-di-1-methylcyclohexyl-[2,2']-diphosphetanyl 1,1'-disulfide, (1R,1R',2R,2R')-1,1'-ethyl-isopropyl-[2,2']-diphosphetanyl 1,1'-disulfide, (1R,1R',2R,2R')-1,1'-ethyl-n-propyl-[2,2']-diphosphetanyl 1,1'-disulfide, (1R,1R',2R,2R')-1,1'-ethyl-isobutyl-[2,2']-diphosphetanyl 1,1'-disulfide, (1R,1R',2R,2R')-1,1'-ethyl-n-butyl-[2,2']-diphosphetanyl 1,1'-disulfide, (1R,1R',2R,2R')-1,1'-ethyl-sec-butyl-[2,2']-diphosphetanyl 1,1'-disulfide, (1R,1R',2R,2R')-1,1'-ethyl-tert-butyl-[2,2']-diphosphetanyl 1,1'-disulfide, (1R,1R',2R,2R')-1,1'-di-tert-butyl-[2,2']-diphosphetanyl 1,1'-dioxide, (1R,1R',2R,2R')-1,1'-di-ethyl-[2,2']-diphosphetanyl 1,1'-dioxide, (1R,1R',2R,2R')-1,1'-di-isopropyl-[2,2']-diphosphetanyl 1,1'-dioxide, (1R,1R',2R,2R')-1,1'-di-n-propyl-[2,2']-diphosphetanyl 1,1'-dioxide, (1R,1R',2R,2R')-1,1'-di-isobutyl-[2,2']-diphosphetanyl 1,1'-dioxide, (1R,1R',2R,2R')-1,1'-di-n-butyl-[2,2']-diphosphetanyl 1,1'-dioxide, (1R,1R',2R,2R')-1,1'-di-isoheptyl-[2,2']-diphosphetanyl 1,1'-dioxide, (1R,1R',2R,2R')-1,1'-di-n-heptyl-[2,2']-diphosphetanyl 1,1'-dioxide, (1R,1R',2R,2R')-1,1'-di-isohexyl-[2,2']-diphosphetanyl 1,1'-dioxide, (1R,1R',2R,2R')-1,1'-di-n-hexyl-[2,2']-diphosphetanyl 1,1'-dioxide, (1R,1R',2R,2R')-1,1'-di-cyclopentyl-[2,2']-diphosphetanyl 1,1'-dioxide, (1R,1R',2R,2R')-1,1'-di-cyclohexyl-[2,2']-diphosphetanyl 1,1'-dioxide, (1R,1R',2R,2R')-1,1'-di-1-methylcyclohexyl-[2,2']-diphosphetanyl 1,1'-dioxide, (1R,1R',2R,2R')-1,1'-ethyl-isopropyl-[2,2']-diphosphetanyl 1,1'-dioxide, (1R,1R',2R,2R')-1,1'-ethyl-n-propyl-[2,2']-diphosphetanyl 1,1'-dioxide, (1R,1R',2R,2R')-1,1'-ethyl-isobutyl-[2,2']-diphosphetanyl 1,1'-dioxide, (1R,1R',2R,2R')-1,1'-ethyl-n-butyl-[2,2']-diphosphetanyl 1,1'-dioxide, (1R,1R',2R,2R')-1,1'-ethyl-sec-butyl-[2,2']-diphosphetanyl 1,1'-dioxide, (1R,1R',2R,2R')-1,1'-ethyl-tert-butyl-[2,2']-diphosphetanyl 1,1'-dioxide, (1S,1'S,2R,2'R)-1,1'-di-tert-butyl-[2,2']-diphosphetanyl 1,1'-diboranate, (1S,1'S,2R,2'R)-1,1'-di-ethyl-[2,2']-diphosphetanyl 1,1'-diboranate, (1S,1'S,2R,2'R)-1,1'-di-isopropyl-[2,2']-diphosphetanyl 1,1'-diboranate, (1S,1'S,2R,2'R)-1,1'-di-n-propyl-[2,2']-diphosphetanyl 1,1'-diboranate, (1S,1'S,2R,2'R)-1,1'-di-isobutyl-[2,2']-diphosphetanyl 1,1'-diboranate, (1S,1'S,2R,2'R)-1,1'-di-n-butyl-[2,2']-diphosphetanyl 1,1'-diboranato, (1S,1'S,2R,2'R)-1,1'-di-isoheptyl-[2,2']-diphosphetanyl 1,1'-diboranate, (1S,1'S,2R,2'R)-1,1'-di-n-heptyl-[2,2']-diphosphetanyl 1,1'-diboranate, (1S,1'S,2R,2'R)-1,1'-di-isohexyl-[2,2']-diphosphetanyl 1,1'-diboranate, (1S,1'S,2R,2'R)-1,1'-di-n-hexyl-[2,2']-diphosphetanyl 1,1'-diboranate, (1S,1'S,2R,2'R)-1,1'-di-cyclopentyl-[2,2']-diphosphetanyl 1,1'-diboranate, (1S,1'S,2R,2'R)-1,1'-di-cyclohexyl-[2,2']-diphosphetanyl 1,1'-diboranate, (1S,1'S,2R,2'R)-1,1'-di-1-methylcyclohexyl-[2,2']-diphosphetanyl 1,1'-diboranate, (1S,1'S,2R,2'R)-1,1'-ethyl-isopropyl-[2,2']-diphosphetanyl 1,1'-diboranate, (1S,1'S,2R,2'R)-1,1'-ethyl-n-propyl-[2,2']-diphosphetanyl 1,1'-diboranate, (1S,1'S,2R,2'R)-1,1'-ethyl-isobutyl-[2,2']-diphosphetanyl 1,1'-diboranate, (1S,1'S,2R,2'R)-1,1'-ethyl-n-butyl-[2,2']-diphosphetanyl 1,1'-diboranate, (1S,1'S,2R,2'R)-1,1'-ethyl-sec-butyl-[2,2']-diphosphetanyl 1,1'-diboranate, and (1S,1'S,2R,2'R)-1,1'-ethyl-tert-butyl-[2,2']-diphosphetanyl 1,1'-diboranate.

Examples of the phosphorus heterocyclic compound dimer represented by formula (4) include five-membered heterocyclic ring compounds, such as (1R,1R',2R,2R')-1,1'-di-tert-butyl-[2,2']-diphosphoranyl 1,1'-disulfide, (1R,1R',2R,2R')-1,1'-di-ethyl-[2,2']-diphosphoranyl 1,1'-disulfide, (1R,1R',2R,2R')-1,1'-di-isopropyl-[2,2'1-diphosphoranyl 1,1'-disulfide, (1R,1R',2R,2R')-1,1'-di-n-propyl-[2,2']-diphosphoranyl 1,1'-disulfide, (1R,1R',2R,2R')-1,1'-diisobutyl-[2,2']-diphosphoranyl 1,1'-disulfide, (1R,1R',2R, 2R')-1,1'-di-n-butyl-[2,2']-diphosphoranyl 1,1'-disulfide, (1R,1R',2R,2R')-1,1'-di-isoheptyl-[2,2']-diphosphoranyl 1,1'-disulfide, (1R,1R',2R,2R')-1,1'-di-n-heptyl-[2,2']-diphosphoranyl 1,1'-disulfide, (1R,1R',2R,2R')-1,1'-di-isohexyl-[2,2']-diphosphoranyl 1,1'-disulfide, (1R,1R',2R,2R')-1,1'-di-n-hexyl-[2,2']-diphosphoranyl 1,1'-disulfide, (1R,1R',2R,2R')-1,1'-di-cyclopentyl-[2,2']-diphosphoranyl 1,1'-disulfide, (1R,1R',2R,2R')-1,1'-di-cyclohexyl-[2,2']-diphosphoranyl 1,1'-disulfide, (1R,1R',2R,2R')-1,1'-di-1-methylcyclohexyl-[2,2']-diphosphoranyl 1,1'-disulfide, (1R,1R',2R,2R')-1,1'-ethyl-iso-propyl-[2,2']-diphosphoranyl 1,1'-disulfide, (1R,1R',2R,2R')-1,1'-ethyl-n-propyl-[2,2']-diphosphoranyl 1,1'-disulfide, (1R,1R',2R,2R')-1,1'-ethyl-isobutyl-[2,2']-diphosphoranyl 1,1'-disulfide, (1R,1R',2R, 2R')-1,1'-ethyl-n-butyl-[2,2']-diphosphoranyl 1,1'-disulfide, (1R,1R',2R,2R')-1,1'-ethyl-sec-butyl-[2,2']-diphosphoranyl 1,1'-disulfide, (1R,1R',2R,2R')-1,1'-ethyl-tert-butyl-[2,2']-diphosphoranyl 1,1'-disulfide, (1R,1R',2R,2R')-1,1'-di-tert-butyl-[2,2']-diphosphoranyl 1,1'-dioxide, (1R,1R',2R,2R')-1, 1'-di-ethyl-[2,2']-diphosphoranyl 1,1'-dioxide, (1R,1R',2R, 2R')-1,1'-di-isopropyl-[2,2']-diphosphoranyl 1,1'-dioxide, (1R,1R',2R,2R')-1,1'-di-n-propyl-[2,2']-diphosphoranyl 1,1'-dioxide, (1R,1R',2R,2R')-1,1-di-isobutyl-[2,2']-diphosphoranyl 1,1'-dioxide, (1R,1R',2R,2R')-1,1'-di-n-butyl-[2,2']-diphosphoranyl 1,1'-dioxide, (1R,1R',2R,2R')-1,1'-di-isoheptyl-[2,2']-diphosphoranyl 1,1'-dioxide, (1R,1R',2R, 2R')-1,1'-di-n-heptyl-[2,2']-diphosphoranyl 1,1'-dioxide, (1R,1R',2R,2R')-1,1'-di-isohexyl-[2,2']-diphosphoranyl 1,1'-dioxide, (1R,1R',2R,2R')-1,1'-di-n-hexyl-[2,2']-diphosphoranyl 1,1'-dioxide, (1R,1R',2R,2R')-1,1'-di-cyclopentyl-[2, 2']-diphosphoranyl 1,1'-dioxide, (1R,1R',2R,2R')-1,1'-di-cyclohexyl-[2,2']-diphosphoranyl 1,1'-dioxide, (1R,1R',2R, 2R')-1,1'-di-1-methylcyclohexyl-[2,2']-diphosphoranyl 1,1'-dioxide, (1R,1R',2R,2R')-1,1'-ethyl-isopropyl-[2,2']-diphosphoranyl 1,1'-dioxide, (1R,1R',2R,2R')-1,1'-ethyl-n-propyl-[2,2']-diphosphoranyl 1,1-dioxide, (1R,1R',2R,2R')-1,1'-ethyl-isobutyl-[2,2']-diphosphoranyl 1,1'-dioxide, (1R, 1R',2R,2R')-1,1'-ethyl-n-butyl-[2,2']-diphosphoranyl 1,1'-dioxide, (1R,1R',2R,2R')-1,1'-ethyl-sec-butyl-[2,2']-diphosphoranyl 1,1'-dioxide, (1R,1R',2R,2R')-1,1'-ethyl-tert-butyl-[2,2']-diphosphoranyl 1,1'-dioxide, (1S,1'S,2R, 2'R)-1,1'-di-tert-butyl-[2,2']-diphosphoranyl 1,1'-diboranate, (1S,1'S,2R,2'R)-1,1'-di-ethyl-[2,2']-diphosphoranyl 1,1'-diboranate, (1S,1'S,2R,2'R)-1,1'-di-isopropyl-[2,2']-diphosphoranyl 1,1'-diboranate, (1S,1'S,2R,2'R)-1,1'-di-n-propyl-[2,2']-diphosphoranyl 1,1'-diboranate, (1S,1'S,2R,2'R)-1,1'-di-isobutyl-[2,2']-diphosphoranyl 1,1'-diboranate, (1S,1'S, 2R,2'R)-1,1'-di-n-butyl-[2,2']-diphosphoranyl 1,1'-diboranate, (1S,1'S,2R,2'R)-1,1'-di-isoheptyl-[2,2']-diphosphoranyl 1,1'-diboranate, (1S,1'S,2R,2'R)-1,1'-di-n-heptyl-[2,2']-diphosphoranyl 1,1'-diboranate, (1S,1'S,2R, 2'R)-1,1'-di-isohexyl-[2,2']-diphosphoranyl 1,1'-diboranate, (1S,1'S,2R,2'R)-1,1'-di-n-hexyl-[2,2']-diphosphoranyl 1,1'-diboranate, (1S,1'S,2R,2'R)-1,1'-di-cyclopentyl-[2,2']-diphosphoranyl 1,1'-diboranate, (1S,1'S,2R,2'R)-1,1'-di-cyclohexyl-[2,2']-diphosphoranyl 1,1'-diboranate, (1S,1'S,2R, 2'R)-1,1'-di-1-methylcyclohexyl-[2,2']-diphosphoranyl 1,1'-diboranate, (1S,1'S,2R,2'R)-1,1'-ethyl-isopropyl-[2,2']-diphosphoranyl 1,1'-diboranate, (1S,1'S,2R,2'R)-1,1'-ethyl-n-propyl-[2,2']-diphosphoranyl 1,1'-diboranate, (1S,1'S,2R, 2'R)-1,1'-ethyl-isobutyl-[2,2']-diphosphoranyl 1,1'-diboranate, (1S,1'S,2R,2'R)-1,1'-ethyl-n-butyl-[2,2']-diphosphoranyl 1,1'-diboranate, (1S,1'S,2R,2'R)-1,1'-ethyl-sec-butyl-[2,2']-diphosphoranyl 1,1'-diboranate, and (1S,1'S, 2R,2'R)-1,1'-ethyl-tert-butyl-[2,2']-diphosphoranyl 1,1'-diboranate.

Examples of the phosphorus heterocyclic compound dimer represented by formula (4) include six-membered heterocyclic compounds, such as (1R,1R',2R,2R')-1,1'-di-tert-butyl-[2,2']-diphosphinanyl 1,1'-disulfide, (1R,1R',2R,2R')-1,1'-di-ethyl-[2,2']-diphosphinanyl 1,1'-disulfide, (1R,1R',2R,2R')-1,1'-di-isopropyl-[2,2']-diphosphinanyl 1,1'-disulfide, (1R, 1R',2R,2R')-1,1'-di-n-propyl-[2,2']-diphosphinanyl 1,1'-disulfide, (1R,1R',2R,2R')-1,1'-di-isobutyl-[2,2']-diphosphinanyl 1,1'-disulfide, (1R,1R',2R,2R')-1,1'-di-n-butyl-[2,2']-diphosphinanyl 1,1'-disulfide, (1R,1R',2R,2R')-1,1'-di-isoheptyl-[2,2']-diphosphinanyl 1,1'-disulfide, (1R,1R',2R, 2R')-1,1'-di-n-heptyl-[2,2']-diphosphinanyl 1,1'-disulfide, (1R,1R',2R,2R')-1,1'-di-isohexyl-[2,2']-diphosphinanyl 1,1'-disulfide, (1R,1R',2R,2R')-1,1'-di-n-hexyl-[2,2']-diphosphinanyl 1,1'-disulfide, (1R,1R',2R,2R')-1,1'-di-cyclopentyl-[2, 2']-diphosphinanyl 1,1'-disulfide, (1R,1R',2R,2R')-1,1'-di-cyclohexyl-[2,2']-diphosphinanyl 1,1'-disulfide, (1R,1R',2R, 2R')-1,1'-di-1-methylcyclohexyl-[2,2']-diphosphinanyl 1,1'-disulfide, (1R,1R',2R,2R')-1,1'-ethyl-isopropyl-[2,2']-diphosphinanyl 1,1'-disulfide, (1R,1R',2R,2R')-1,1'-ethyl-n-propyl-[2,2']-diphosphinanyl 1,1'-disulfide, (1R,1R',2R, 2R')-1,1'-ethyl-isobutyl-[2,2']-diphosphinanyl 1,1'-disulfide, (1R,1R',2R,2R')-1,1'-ethyl-n-butyl-[2,2']-diphosphinanyl 1,1'-disulfide, (1R,1R',2R,2R')-1,1'-ethyl-sec-butyl-[2,2']-diphosphinanyl 1,1'-disulfide, (1R,1R',2R,2R')-1,1'-ethyl-tert-butyl-[2,2']-diphosphinanyl 1,1'-disulfide, (1R,1R',2R, 2R')-1,1'-di-tert-butyl-[2,2']-diphosphinanyl 1,1'-dioxide, (1R,1R',2R,2R')-1,1'-di-ethyl-[2,2']-diphosphinanyl 1,1'-dioxide, (1R,1R',2R,2R')-1,1'-di-isopropyl-[2,2']-diphosphinanyl 1,1'-dioxide, (1R,1R',2R,2R')-1,1'-di-n-propyl-[2,2']-diphosphinanyl 1,1'-dioxide, (1R,1R',2R,2R')-1,1'-di-isobutyl-[2,2']-diphosphinanyl 1,1'-dioxide, (1R,1R',2R, 2R')-1,1'-di-n-butyl-[2,2']-diphosphinanyl 1,1'-dioxide, (1R, 1R',2R,2R')-1,1'-di-isoheptyl-[2,2']-diphosphinanyl 1,1'-dioxide, (1R,1R',2R,2R')-1,1'-di-n-heptyl-[2,2']-diphosphinanyl 1,1'-dioxide, (1R,1R',2R,2R')-1,1'-di-isohexyl-[2,2']-diphosphinanyl 1,1'-dioxide, (1R,1R', 2R,2R')-1,1'-di-n-hexyl-[2,2']-diphosphinanyl 1,1'-dioxide, (1R, 1R',2R,2R')-1,1'-di-cyclopentyl-[2,2']-diphosphinanyl 1,1'-dioxide, (1R,1R',2R,2R')-1,1'-di-cyclohexyl-[2,2']-diphosphinanyl 1,1'-dioxide, (1R,1R',2R,2R')-1,1'-di-1-methylcyclohexyl-[2,2']-diphosphinanyl 1,1'-dioxide, (1R, 1R',2R,2R')-1,1'-ethyl-isopropyl-[2,2']-diphosphinanyl 1,1'-dioxide, (1R,1R',2R,2R')-1,1'-ethyl-n-propyl-[2,2']-diphosphinanyl. 1,1'-dioxide, (1R,1R',2R,2R')-1,1'-ethyl-isobutyl-[2,2']-diphosphinanyl 1,1'-dioxide, (1R,1R',2R, 2R')-1,1'-ethyl-n-butyl-[2,2']-diphosphinanyl 1,1'-dioxide, (1R,1R',2R,2R')-1,1'-ethyl-sec-butyl-[2,2']-diphosphinanyl 1,1'-dioxide, (1R,1R',2R,2R')-1,1'-ethyl-tert-butyl-[2,2']-diphosphinanyl 1,1'-dioxide, (1S,1'S,2R,2'R)-1,1'-di-tert-butyl-[2,2']-diphosphinanyl 1,1'-diboranate, (1S,1'S,2R,2'R)-1, 1'-di-ethyl-[2,2']-diphosphinanyl 1,1'-diboranate, (1S,1'S, 2R,2'R)-1,1'-di-isopropyl-[2,2']-diphosphinanyl 1,1'-diboranate, (1S,1'S,2R,2'R)-1,1'-di-n-propyl-[2,2']-diphosphinanyl 1,1'-diboranate, (1S,1'S,2R,2'R)-1,1'-di-isobutyl-[2,2']-diphosphinanyl 1,1'-diboranate, (1S,1'S,2R, 2'R)-1,1'-di-n-butyl-[2,2']-diphosphinanyl 1,1'-diboranate, (1S,1'S,2R,2'R)-1,1'-di-isoheptyl-[2,2']-diphosphinanyl 1,1'-diboranate, (1S,1'S,2R,2'R)-1,1'-di-n-heptyl-[2,2']-diphosphinanyl 1,1'-diboranate, (1S,1'S,2R,2'R)-1,1'-di-isohexyl-[2,2']-diphosphinanyl 1,1'-diboranate, (1S,1'S,2R,2'R)-1,1'-di-n-hexyl-[2,2']-diphosphinanyl 1,1'-diboranate, (1S,1'S, 2R,2'R)-1,1'-di-cyclopentyl-[2,2']-diphosphinanyl 1,1'-diboranate, (1S,1'S,2R,2'R)-1,1'-di-cyclohexyl-[2,2']-diphosphinanyl 1,1'-diboranate, (1S,1'S,2R,2'R)-1,1'-di-1-methylcyclohexyl-[2,2']-diphosphinanyl 1,1'-diboranate, (1S,1'S,2R,2'R)-1,1'-ethyl-isopropyl-[2,2']-diphosphinanyl 1,1'-diboranate, (1S,1'S,2R,2'R)-1,1'-ethyl-n-propyl-[2,2']-diphosphinanyl 1,1'-diboranate, (1S,1'S,2R,2'R)-1,1'-ethyl-isobutyl-[2,2']-diphosphinanyl 1,1'-diboranate, (1S,1'S,2R,2'R)-1,1'-ethyl-n-butyl-[2,2']-diphosphinanyl 1,1'-diboranatoe, (1S,1'S,2R,2'R)-1,1'-ethyl-sec-butyl-[2,2']-diphosphinanyl 1,1'-diboranate, and (1S,1'S,2R,2'R)-1,1'-ethyl-tert-butyl-[2,2']-diphosphinanyl 1,1'-diboranate.

Examples of the phosphorus heterocyclic compound dimer represented by formula (4) include seven-membered heterocyclic compounds, such as (1R,1R',2R,2R')-1,1'-di-tert-butyl-[2,2']-diphosphepanyl 1,1'-disulfide, (1R,1R',2R,2R')-1,1'-di-ethyl-[2,2']-diphosphepanyl 1,1'-disulfide, (1R,1R',2R,2R')-1,1'-di-isopropyl-[2,2']-diphosphepanyl 1,1'-disulfide, (1R,1R',2R,2R')-1,1'-di-n-propyl-[2,2']-diphosphepanyl 1,1'-disulfide, (1R,1R',2R,2R')-1,1'-di-isobutyl-[2,2']-diphosphepanyl 1,1'-disulfide, (1R,1R',2R,2R')-1,1'-di-n-butyl-[2,2']-diphosphepanyl 1,1'-disulfide, (1R,1R',2R,2R')-1,1'-di-isoheptyl-[2,2']-diphosphepanyl 1,1'-disulfide, (1R,1R',2R,2R')-1,1'-di-n-heptyl-[2,2']-diphosphepanyl 1,1'-disulfide, (1R,1R',2R,2R')-1,1'-di-isohexyl-[2,2']-diphosphepanyl 1,1'-disulfide, (1R,1R',2R,2R')-1,1'-di-n-hexyl-[2,2']-diphosphepanyl 1,1'-disulfide, (1R,1R',2R,2R')-1,1'-di-cyclopentyl-[2,2']-diphosphepanyl 1,1'-disulfide, (1R,1R',2R,2R')-1,1'-di-cyclohexyl-[2,2']-diphosphepanyl 1,1'-disulfide, (1R,1R',2R,2R')-1,1'-di-1-methylcyclohexyl-[2,2']-diphosphepanyl 1,1'-disulfide, (1R,1R',2R,2R')-1,1'-ethyl-isopropyl-[2,2']-diphosphepanyl 1,1'-disulfide, (1R,1R',2R,2R')-1,1'-ethyl-n-propyl-[2,2']-diphosphepanyl 1,1'-disulfide, (1R,1R',2R,2R')-1,1'-ethyl-isobutyl-[2,2']-diphosphepanyl 1,1'-disulfide, (1R,1R',2R,2R')-1,1'-ethyl-n-butyl-[2,2']-diphosphepanyl 1,1'-disulfide, (1R,1R',2R,2R')-1,1'-ethyl-sec-butyl-[2,2']-diphosphepanyl 1,1'-disulfide, (1R,1R',2R,2R')-1,1'-ethyl-tert-butyl-[2,2']-diphosphepanyl 1,1'-disulfide, (1R,1R',2R,2R')-1,1'-di-tert-butyl-[2,2']-diphosphepanyl 1,1'-dioxide, (1R,1R',2R,2R')-1,1'-di-ethyl-[2,2']-diphosphepanyl 1,1'-dioxide, (1R,1R',2R,2R')-1,1'-di-isopropyl-[2,2']-diphosphepanyl 1,1'-dioxide, (1R,1R',2R,2R')-1,1'-di-n-propyl-[2,2']-diphosphepanyl 1,1'-dioxide, (1R,1R',2R,2R')-1,1'-di-isobutyl-[2,2']-diphosphepanyl 1,1'-dioxide, (1R,1R',2R,2R')-1,1'-di-n-butyl-[2,2']-diphosphepanyl 1,1'-dioxide, (1R,1R',2R,2R')-1,1'-di-isoheptyl-[2,2']-diphosphepanyl 1,1'-dioxide, (1R,1R',2R,2R')-1,1'-di-n-heptyl-[2,2']-diphosphepanyl 1,1'-dioxide, (1R,1R',2R,2R')-1,1'-di-isohexyl-[2,2']-diphosphepanyl 1,1'-dioxide, (1R,1R',2R,2R')-1,1'-di-n-hexyl-[2,2']-diphosphepanyl 1,1'-dioxide, (1R,1R',2R,2R')-1,1'-di-cyclopentyl-[2,2']-diphosphepanyl 1,1'-dioxide, (1R,1R',2R,2R')-1,1'-di-cyclohexyl-[2,2']-diphosphepanyl 1,1'-dioxide, (1R,1R',2R,2R')-1,1'-di-1-methylcyclohexyl-[2,2']-diphosphepanyl 1,1'-dioxide, (1R,1R',2R,2R')-1,1'-ethyl-isopropyl-[2,2']-diphosphepanyl 1,1'-dioxide, (1R,1R',2R,2R')-1,1'-ethyl-n-propyl-[2,2']-diphosphepanyl 1,1'-dioxide, (1R,1R',2R,2R')-1,1'-ethyl-isobutyl-[2,2']-diphosphepanyl 1,1'-dioxide, (1R,1R',2R,2R')-1,1'-ethyl-n-butyl-[2,2']-diphosphepanyl 1,1'-dioxide, (1R,1R',2R,2R')-1,1'-ethyl-sec-butyl-[2,2']-diphosphepanyl 1,1'-dioxide, (1R,1R',2R,2R')-1,1'-ethyl-tert-butyl-[2,2']-diphosphepanyl 1,1'-dioxide. (1S,1'S,2R,2'R)-1,1'-di-tert-butyl-[2,2']-diphosphepanyl 1,1'-diboranate, (1S,1'S,2R,2'R)-1,1'-di-ethyl-[2,2']-diphosphepanyl 1,1'-diboranate, (1S,1'S,2R,2'R)-1,1'-di-isopropyl-[2,2']-diphosphepanyl 1,1'-diboranate, (1S,1'S,2R,2'R)-1,1'-di-n-propyl-[2,2']-diphosphepanyl 1,1'-diboranate, (1S,1'S,2R,2'R)-1,1'-di-isobutyl-[2,2']-diphosphepanyl 1,1'-diboranate, (1S,1'S,2R,2'R)-1,1'-di-n-butyl-[2,2']-diphosphepanyl 1,1'-diboranate, (1S,1'S,2R,2'R)-1,1'-di-isoheptyl-[2,2']-diphosphepanyl 1,1'-diboranate, (1S,1'S,2R,2'R)-1,1'-di-n-heptyl-[2,2']-diphosphepanyl 1,1'-diboranate, (1S,1'S,2R,2'R)-1,1'-di-isohexyl-[2,2']-diphosphepanyl 1,1'-diboranate, (1S,1'S,2R,2'R)-1,1'-di-n-hexyl-[2,2']-diphosphepanyl 1,1'-diboranate, (1S,1'S,2R,2'R)-1,1'-di-cyclopentyl-[2,2']-diphosphepanyl 1,1'-diboranate, (1S,1'S,2R,2'R)-1,1'-di-cyclohexyl-[2,2']-diphosphepanyl 1,1'-diboranate, (1S,1'S,2R,2'R)-1,1'-di-1-methylcyclohexyl-[2,2']-diphosphepanyl 1,1'-diboranate, (1S,1'S,2R,2'R)-1,1'-ethyl-isopropyl-[2,2']-diphosphepanyl 1,1'-diboranate, (1S,1'S,2R,2'R)-1,1'-ethyl-n-propyl-[2,2']-diphosphepanyl 1,1'-diboranate, (1S,1'S,2R,2'R)-1,1'-ethyl-isobutyl-[2,2']-diphosphepanyl 1,1'-diboranate, (1S,1'S,2R,2'R)-1,1'-ethyl-n-butyl-[2,2']-diphosphepanyl 1,1'-diboranate, (1S,1'S,2R,2'R)-1,1'-ethyl-sec-butyl-[2,2']-diphosphepanyl 1,1'-diboranate, and (1S,1'S,2R,2'R)-1,1'-ethyl-tert-butyl-[2,2']-diphosphepanyl 1,1'-diboranate.

<Third Step>

In the third step, borane, oxygen, or sulfur is removed from the phosphorus heterocyclic compound dimer represented by formula (4).

In the present invention, "borane removal" means removal of a boranato group bonded to a lone electron pair of each phosphorus atom of the compound represented by formula (4). A method for removing a boranato group is not particularly limited, and any general method for removing borane may be used. For example, a method of heating in an amine solvent, a method of reacting with a superstrong acid such as trifluoromethanesulfonic acid or the like and then neutralizing with an alkali, or the like may be used. In the method of heating in an amine solvent, the reaction temperature is 50 to 80° C. and preferably 60 to 70° C. With the temperature lower than 50° C., the reaction rate is low, while with the temperature over 80° C., optical purity decreases. The reaction time is preferably 1 to 3 hours.

In the present invention, "deoxidation" means removal of an oxygen atom bonded to a lone electron pair of each phosphorus atom of the compound represented by formula (4), and is reduction reaction. The reduction reaction is not particularly limited, and any general reduction reaction can be used. For example, trichlorosilane, phenylsilane, or the like can be used.

In the present invention, "desulfurization" means removal of a sulfur atom bonded to a lone electron pair of each phosphorus atom of the compound represented by formula (4), and is reduction reaction. The reduction reaction is not particularly limited, and any general reduction reaction can be used. For example, a reduction method using hexachlorodisilane, a reduction method using Raney nickel, or the like can be used. In the reduction method using hexachlorodisilane, the reaction temperature is 20 to 90° C. and preferably 80 to 90° C., and the reaction time is 1 to 6 hours.

As described above, borane removal, deoxidization, or desulfurization of the phosphorus heterocyclic compound dimer represented by formula (4) can produce an optically active phosphorus heterocyclic dimer represented by formula (5) while maintaining the configuration at each phosphorus atom. Therefore, the dimer of formula (4) is a compound suitable for producing the compound of formula (5).

The configurations of the compound of formulae (5) and the compound of formula (4) can be confirmed by single-crystal X-ray structural analysis.

The optically active phosphorus heterocyclic dimer produced by the process of the present invention has a configuration represented by formula (5):

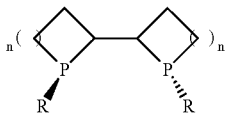

(5)

In the optically active phosphorus heterocyclic dimer represented by formula (5), R and n represent the same as the above.

In this compound, the phosphorus atom at the 1-position and the carbon atom at the 2-position in each phosphorus-containing heterocyclic skeleton have respective asymmetric points, and the absolute configuration is designated by (1S, 1'S,2R,2R') according to a CIP method. The compound also has the property of being easily-oxidizable.

Examples of the optically active phosphorus heterocyclic dimer represented by formula (5) include four-members phosphorus heterocyclic compounds, such as (1S,1S',2R, 2R')-1,1'-di-tert-butyl-[2,2']-diphosphetane, (1S,1S',2R, 2R')-1,1'-di-ethyl-[2,2']-diphosphetane, (1S,1S',2R,2R')-1, 1'-di-isopropyl-[2,2']-diphosphetane, (1S,1S',2R,2R')-1,1'-di-n-propyl-[2,2']-diphosphetane, (1S,1S',2R,2R')-1,1'-di-isobutyl-[2,2']-diphosphetane, (1S,1S',2R,2R')-1,1'-di-n-butyl-[2,2']-diphosphetane, (1S,1S',2R,2R')-1,1'-di-isoheptyl-[2,2']-diphosphetane, (1S,1S',2R,2R')-1,1'-di-n-heptyl-[2,2']-diphosphetane, (1S,1S',2R,2R')-1,1'-di-isohexyl-[2,2']-diphosphetane, (1S,1S',2R,2R')-1,1'-di-n-hexyl-[2,2']-diphosphetane, (1S,1S',2R,2R')-1,1'-di-cyclopentyl-[2,2']-diphosphetane, (1S,1S',2R,2R')-1,1'-di-cyclohexyl-[2,2']-diphosphetane, (1S,1S',2R,2R')-1,1'-di-1-methylcyclohexyl-[2,2']-diphosphetane, (1S,1S',2R,2R')-1, 1'-ethyl-isopropyl-[2,2']-diphosphetane, (1S,1S',2R,2R')-1, 1'-ethyl-n-propyl-[2,2']-diphosphetane, (1S,1S',2R,2R')-1, 1'-ethyl-isobutyl-[2,2']-diphosphetane, (1S,1S',2R,2R')-1,1'-ethyl-n-butyl-[2,2']-diphosphetane, (1S,1S',2R,2R')-1,1'-ethyl-sec-butyl-[2,2']-diphosphetane, and (1S,1S',2R,2R')-1, 1'-ethyl-tert-butyl-[2,2']-diphosphetane.

Examples of the optically active phosphorus heterocyclic dimer represented by formula (5) include five-members phosphorus heterocyclic compounds, such as (1S,1S',2R,2R')-1, 1'-di-tert-butyl-[2,2']-diphosphorane, (1S,1S',2R,2R')-1,1'-di-ethyl-[2,2']-diphosphorane, (1S,1S',2R,2R')-1,1'-di-isopropyl-[2,2']-diphosphorane, (1S,1S',2R,2R')-1,11-di-n-propyl-[2,2']-diphosphorane, (1S,1S',2R,2R')-1,1'-di-isobutyl-[2,2']-diphosphorane, (1S,1S',2R,2R')-1,1'-di-n-butyl-[2,2']-diphosphorane, (1S,1S',2R,2R')-1,1'-di-isoheptyl-[2,2']-diphosphorane, (1S,1S',2R,2R')-1,1'-di-n-heptyl-[2,2']-diphosphorane, (1S,1S',2R,2R')-1,1'-di-isohexyl-[2,2']-diphosphorane, (1S,1S',2R,2R')-1,1'-di-n-hexyl-[2,2']-diphosphorane, (1S,1S',2R,2R')-1,1'-di-cyclopentyl-[2,2']-diphosphorane, (1S,1S',2R,2R')-1,1'-di-cyclohexyl-[2,2']-diphosphorane, (1S,1S',2R,2R')-1,1'-di-1-methylcyclohexyl-[2,2']-diphosphorane, (1S,1S',2R,2R')-1, 1'-ethyl-isopropyl-[2,2']-diphosphorane, (1S,1S',2R,2R')-1, 1'-ethyl-n-propyl-[2,2']-diphosphorane, (1S,1S',2R,2R')-1, 1'-ethyl-isobutyl-[2,2']-diphosphorane, (1S,1S',2R,2R')-1,1'-ethyl-n-butyl-[2,2']-diphosphorane, (1S,1S',2R,2R')-1,1'-ethyl-sec-butyl-[2,2']-diphosphorane, and (1S,1S',2R,2R')-1, 1'-ethyl-tert-butyl-[2,2']-diphosphorane.

Examples of the optically active phosphorus heterocyclic dimer represented by formula (5) include six-members phosphorus heterocyclic compounds, such as (1S,1S',2R,2R')-1, 1'-di-t-butyl-[2,2']-diphosphinane, (1S,1S',2R,2R')-1,1'-di-ethyl-[2,2']-diphosphinane, (1S,1S',2R,2R')-1,1'-di-isopropyl-[2,2']-diphosphinane, (1S,1S',2R,2R')-1,1'-di-n-propyl-[2,2']-diphosphinane, (1S,1S',2R,2R')-1,1'-di-isobutyl-[2,2']-diphosphinane, (1S,1S',2R,2R')-1,1'-di-n-butyl-[2,2']-diphosphinane, (1S,1S',2R,2R')-1,1'-di-isoheptyl-[2,2']-diphosphinane, (1S,1S',2R,2R')-1,1'-di-n-heptyl-[2,2']-diphosphinane, (1S,1S',2R,2R')-1,1'-di-isohexyl-[2,2']-diphosphinane, (1S,1S',2R,2R')-1,1'-di-n-hexyl-[2,2']-diphosphinane, (1S,1S',2R,2R')-1,1'-di-cyclopentyl-[2,2']-diphosphinane, (1S,1S',2R,2R')-1,1'-di-cyclohexyl-[2,2']-diphosphinane, (1S,1S',2R,2R')-1,1'-di-1-methylcyclohexyl-[2,2']-diphosphinane, (1S,1S',2R,2R')-1, 1'-ethyl-isopropyl-[2,2']-diphosphinane, (1S,1S',2R,2R')-1, 1'-ethyl-n-propyl-[2,2']-diphosphinane, (1S,1S',2R,2R')-1, 1'-ethyl-isobutyl-[2,2']-diphosphinane, (1S,1S',2R,2R')-1,1'-ethyl-n-butyl-[2,2']-diphosphinane, (1S,1S',2R,2R')-1,1'-ethyl-sec-butyl-[2,2']-diphosphinane, and (1S,1S', 2R,2R')-1,1'-ethyl-tert-butyl-[2,2']-diphosphinane.

Examples of the optically active phosphorus heterocyclic dimer represented by formula (5) include seven-members phosphorus heterocyclic compounds, such as (1S,1S',2R, 2R')-1,1'-di-tert-butyl-[2,2']-diphosphepane, (1S,1S',2R, 2R')-1,1'-di-ethyl-[2,2']-diphosphepane, (1S,1S',2R,2R')-1, 1'-di-isopropyl-[2,2']-diphosphepane, (1S,1S',2R,2R')-1,1'-di-n-propyl-[2,2']-diphosphepane, (1S,1S',2R,2R')-1,1'-di-isobutyl-[2,2']-diphosphepane, (1S,1S',2R,2R')-1,1'-di-n-butyl-[2,2']-diphosphepane, (1S,1S',2R,2R')-1,1'-di-isoheptyl-[2,2']-diphosphepane, (1S,1S',2R,2R')-1,1'-di-n-heptyl-[2,2']-diphosphepane, (1S,1S',2R,2R')-1,1'-di-isohexyl-[2,2']-diphosphepane, (1S,1S',2R,2R')-1,1'-di-n-hexyl-[2,2']-diphosphepane, (1S,1S',2R,2R')-1,1'-di-cyclopentyl-[2,2']-diphosphepane, (1S,1S',2R,2R')-1,1'-di-cyclohexyl-[2,2']-diphosphepane, (1S,1S',2R,2R')-1,1'-di-1-methylcyclohexyl-[2,2']-diphosphepane, (1S,1S',2R,2R')-1, 1'-ethyl-isopropyl-[2,2']-diphosphepane, (1S,1S',2R,2R')-1, 1'-ethyl-n-propyl-[2,2']-diphosphepane, (1S,1S',2R,2R')-1, 1'-ethyl-isobutyl-[2,2']-diphosphepane, (1S,1S',2R,2R')-1, 1'-ethyl-n-butyl-[2,2']-diphosphepane, (1S,1S',2R,2R')-1,1'-ethyl-sec-butyl-[2,2']-diphosphepane, and (1S,1S',2R,2R')-1,1'-ethyl-tert-butyl-[2,2']-diphosphepane.

The optically active phosphorus heterocyclic dimer represented by formula (5) can be reacted with a transition metal complex represented by formula (6):

$$[M(A)p(B)q]n \qquad (6)$$

to produce a transition metal complex having the compound of formula (5) as a ligand in the reaction system. The resulting transition metal complex can be used in catalytic asymmetric synthesis reaction.

In formula (6), M is a transition metal serving as a central metal of the transition metal complex and is preferably rhodium, ruthenium, palladium, or copper.

In formula (6), A is a ligand of the transition metal complex and is an electron-donating ligand which is exchanged with the compound of formula (5) serving as a ligand in the reaction system. From the viewpoint of easy ligand exchange and easy production of an asymmetric metal complex having the compound of formula (5) as a ligand in the reaction system, ethylene, a hydrocarbon diene, a carbonyl group, allyl anion, or 2-methylallyl anion is particularly preferred. Examples of the hydrocarbon diene include cycloocta-1,5-diene (also referred to as "cod" hereinafter), norbornadiene (also referred to as "nbd" hereinafter), and the like.

In formula (6), B is a ligand of the transition metal complex and is a ligand which is not exchanged with the compound of formula (5) serving as a ligand. Examples of B include a fluorine atom, a bromine atom, an iodine atom, an acetoxyl group (also referred to as "OAc" hereinafter), a trifluoromethanesulfonyloxy group (also referred to as "OTf" hereinafter), a nitrile group, and dimethylformamide.

In formula (6), p represents an integer of 0 to 2, q represents an integer of 0 to 2, (p+q) is 1 or more, and n represents an integer of 1 or 2. However, these numbers vary depending on the type and valency of the central metal M. When p is 1 or 2, for example, Rh[(cod)Cl]$_2$ produces a transition metal complex by ligand exchange of the compound of formula (5) with cod. When p is 0, for example, Cu(OTf)$_2$ produces a transition metal complex by direct coordination of the compound of formula (1) to copper without ligand exchange.

When the compound of formula (5) is added to a reaction system in which the transition metal complex of formula (6) is present, a transition metal complex is produced by ligand exchange or direct coordination in the reaction system. The resultant transition metal complex can be used in catalytic asymmetric synthesis reaction because the compound of formula (5) serving as a ligand creates an effective asymmetric space.

An example of the asymmetric synthesis reaction using the transition metal complex produced in the reaction system is asymmetric reduction reaction.

When the compound of formula (5) and the transition metal complex of formula (6) are present in the same reaction system, a transition metal complex is rapidly produced. Therefore, asymmetric reduction reaction can be performed by a method in which the compound of formula (5) and the transition metal complex of formula (6) are successively added to, for example, an asymmetric reduction reactor to produce an asymmetric transition metal complex in the reaction system containing raw materials. Alternatively, the compound of formula (5) and the transition metal complex of formula (6) may be mixed to produce a transition metal complex, and then the resulting transition metal complex may be added to an asymmetric reduction reaction system containing raw materials.

The reaction temperature depends on the types of the reaction and raw materials used or the central metal of the transition metal complex used, but the temperature is about −20 to 30° C. With the temperature lower than −20° C., the reaction rate is low, while with the temperature over 30° C., optical purity tends to decrease. The reaction time depends on the types of the reaction and raw materials used or the central metal of the transition metal complex used, but the time is about 1 to 3 hours.

Examples of the solvent used in the reaction include, but are not limited to, saturated hydrocarbons such as hexane; aromatic hydrocarbons such as toluene; alcohols such as methanol; ethers such as diethyl ether and THF; halogenated hydrocarbons such as methylene chloride; and nitriles such as acetonitrile. The solvent is preferably dehydrated by an ordinary method before use from the viewpoint of prevention of deactivation of the transition metal complex.

The transition metal complex of the present invention is produced by reaction between the compound of formula (5) and the transition metal complex of formula (6) to have a structure represented by formula (7) or (8):

(7)

(8)

In formula (7), L represents the compound represented by formula (5), which coordinates to the central metal to create an asymmetric space. Furthermore, M, A, B, p, and q represent the same as those of the transition metal complex of formula (6), and the values of p and q vary according to the type and valency of the central metal M.

In formula (8), L represents the compound represented by formula (5), and Y represents a counter anion when the transition metal complex has positive charge. Examples of Y include a tetrafluoroboric acid group ($BF_4^-$), a hexafluorophosphoric cid group ($PF6^-$), and an antimony hexafluoride group ($SbF_6^-$). Furthermore, M, A, and B represent the same as those of the transition metal complex of formula (6), x represents an integer of 1 or 2, r represents an integer of 0 to 2, s represents an integer of 0 to 4, and r+s is 1 or more. The values of x, r, and s vary depending on the type and valency of the central metal M.

Examples of a rhodium complex include [RhCl(L)]$_2$, [RhBr(L)]$_2$, [RhI(L)]$_2$, [Rh(OAc) (L)]$_2$, and the like. Examples of a ruthenium complex include [RuCl$_2$(L)]$_2$, [RuBr$_2$(L)]$_2$, [RuCl$_2$(L)(DMF)]$_2$, [Ru$_2$Cl$_4$(L)$_2$]NEt$_3$, and the like. Examples of a palladium complex include [PdCl(L)]$_2$, [PdCl$_2$(L)], [Pd(C$_2$H$_4$)L], and the like. Examples of a copper complex include [Cu(OTf)$_2$(L)], [CuCN(L)], [CuI(L)], and the like.

The transition metal complex of formula (7) or (8) can be produced by a known method, e.g., the method described in "Jikken Kagaku Kouza (4th edition) (Experimental Chemistry) 18, Organometallic Complex", edited by The Chemical Society of Japan, Maruzen, 1991. Examples of a method for producing a rhodium complex include the methods described in "Jikken Kagaku Kouza (4th edition) (Experimental Chemistry) 18, Organometallic Complex", edited by The Chemical Society of Japan, Maruzen, 1991, pp. 327-139, and J. Am. Chem. Soc., 1994, 116, pp. 4062-4066. Examples of a method for producing a ruthenium complex include the method described in "Gosei-Kagakusha No Tameno Jikken Yuki-Kinzoku-Kagaku (Experimental Organic Chemistry for Synthetic Chemists)" edited by Kodansha Scientific, pp. 391-411, Maruzen, 1991. Examples of a method for producing a copper complex include the method described in "Jikken Kagaku Kouza (4th edition) (Experimental Chemistry) 18, Organometallic Complex", edited by The Chemical Society of Japan, Maruzen, 1991, pp. 440-450.

For example, a THF solution of the compound of formula (5) is added to a THF solution of bis(cycloocta-1,5-diene) rhodium(I) tetrafluoroborate to produce [Rh(cycloocta-1,5-diene) (L)]$^+$BF$_4^-$ by ligand exchange. The resultant rhodium complex having the compound of formula (5) as a ligand can be confirmed by the chemical shift and coupling constant obtained from $^{31}$P-NMR analysis.

The transition metal complex of formula (7) or (8) contains the compound of formula (5) serving as a ligand which creates an effective asymmetric space, and is thus suitable for catalytic asymmetric synthesis reaction. Therefore, the transition metal complex of formula (7) or (8) can satisfactorily produce catalytic asymmetric reduction reaction. The reaction raw materials, reducing agent, and nucleophilic agent used, and the solvent, reaction temperature, and reaction time used are the same as those for producing the transition metal complex in the above-descried reaction system.

EXAMPLES

The present invention will be described in detail below with reference to examples, but the present invention is not limited to these examples.

Example 1

Synthesis of 1-tert-butyl-phosphetane 1-sulfide

The inside of a well-dried 2-L flask was sufficiently replaced with argon, and 150.2 g (200 mmol) of a 12% n-hexane solution of tert-butyl phosphine and 18.9 mL (200 mmol) of 1,3-dichloropropane were charged in the flask. Then, 1 L of a THF solvent was added to the flask, followed by cooling to −78° C. To the flask, 277 mL (440 mmol) of n-butyl lithium at a concentration of 1.59 mol/L over was added dropwise 1 hour using a dropping funnel. After the reaction solution was stirred at −78° C. for 1 hour, the solution was heated to 0° C., and 9.6 g (300 mmol) of sulfur powder was added to the solution at a time. After stirring at room temperature for 2 hours, 200 mL of pure water was carefully added to terminate reaction. An aqueous layer was separated, and an organic layer was washed with 200 mL of pure water and 200 mL of saturated brine and dehydrated over anhydrous sodium sulfate. Then, the solvent was distilled off, and the resulting crude product was purified by an alumina column and recrystallized from hexane to obtain 15.6 g of target 1-tert-butyl-phosphetane 1-sulfide. The yield was 48%.

Physical Property Data
    Melting point: 120.0-120.8° C.
    $^1$H NMR (CDCl$_3$) δ1.30 (d, $^3J_{HP}$=16.4 Hz, 9H), 1.95-2.15 (m, 2H), 2.25-2.65 (m, 1H), 2.45-2.65 (m, 2H), 2.60-2.80 (m, 2H) $^{13}$C NMR δ14.15 (d, $^2J_{CP}$=21.1 Hz), 23.86 (d, $^2J_{CP}$=2.7 Hz), 30.97 (d, $J_{CP}$=45.35 Hz), 33.92 (d, $J_{CP}$=34.71 Hz) $^{31}$P NMR (1H decoupled, CDCl$_3$) δ82.07 (s)
    IR (KBr) 2960, 1462, 1362, 945, 718, 678 cm$^{-1}$
    HRMS calculated value (C$_7$H$_{15}$PS (M$^+$)) 162.0632, observed value 162.0631

Example 2

Synthesis of 1-boranato-1-tert-butyl-phosphetane

The inside of a well-dried 3-L flask was sufficiently replaced with argon, and 172 g (200 mmol) of a 10.6% n-hexane solution of tert-butyl phosphine and 18.9 mL (200 mmol) of 1,3-dichloropropane were charged in the flask. Then, 1.5 L of a THF solvent was added to the flask, followed by cooling to −78° C. To the flask, 171 mL (420 mmol) of n-butyl lithium at a concentration of 2.45 mol/L was added dropwise using a dropping funnel over 2 hours. The reaction solution was heated to 0° C. over 3 hours under stirring, and 195 mL (220 mmol) of a borane-tetrahydrofuran complex tetrahydrofuran solution at a concentration of 1.13 mol/L was added. After stirring at 0° C. for 1 hour, 200 mL of pure water was carefully added to terminate reaction. An aqueous layer was separated, and an organic layer was washed with 200 mL of pure water, 100 mL of a 1 mol/L aqueous hydrochloric acid solution, and 200 mL of saturated brine, and dehydrated over anhydrous sodium sulfate. Then, the resulting crude product was distilled under reduced pressure to obtain 16.7 g of 1-boranato-1-tert-butyl-phosphetane. The yield was 58%.

Physical Property Data
    Melting point: 91-93° C./6 mmHg
    $^1$HNMR (CDCl$_3$) δ0.67 (br q, $J_{HB}$=95.3 Hz, 3H), 1.22 (d, $^3J_{HP}$=14.0 Hz, 9H), 1.95-2.10 (m, 2H), 2.15-2.30 (m, 2H), 2.30-2.45 (m, 1H), 2.45-2.65 (m, 1H)
    $^{13}$C NMR δ18.00 (d, $J_{CP}$=38.5 Hz), 18.14 (d, $^2J_{CP}$=17.4 Hz), 24.5 (d, $^2J_{CP}$=3.8 Hz), 28.4 (d, $J_{CP}$=19.24 Hz)
    $^{31}$P NMR (1H decoupled, CDCl$_3$) δ65.8 (q, $J_{PB}$=51.3 Hz) GCMS 143 (M−H)$^+$

Example 3

Synthesis of (1R,1R',2R,2R')-1,1'-di-tert-butyl-[2,2']-diphosphetanyl 1,1'-disulfide The inside of a well-dried 300-mL two-necked flask was sufficiently replaced with argon, and 8.44 g (36 mmol) of sparteine and then 70 mL of dry ether were added using a syringe, followed by stirring. After cooling to −78° C. in a dry ice/methanol bath, s-BuLi (36 mmol) was added to the resultant mixture using a syringe, followed by stirring for 1 hour. To the flask, a solution of 4.87 g (30 mmol) of 1-tert-butyl-phosphetane 1-sulfide prepared in Example 1 in 30 mL of dehydrated toluene was added using a dropping funnel at a reaction temperature kept at −78° C. The dropping time was 1 hour. After the dropping was completed, the reaction solution was stirred at −78° C. for 5 hours, and then 6.05 g (45 mmol) of copper chloride was added at a time. After the flask was returned to room temperature over 2 hours, the solution was further stirred at room temperature for 12 hours. After the stirring, 150 mL of 25% ammonia water was added to terminate reaction. Furthermore, 100 mL of ethyl acetate was added for a separation operation. An aqueous layer was subjected to three times of extraction with 100 mL of ethyl acetate each, and the collected organic layers were washed with 5% ammonia, 2M HCl, pure water, and brine, dehydrated over anhydrous sodium sulfate, and then concentrated.

The concentrate was roughly purified by a short column (silica gel, ethyl acetate) and then purified by flash chromatography (silica gel, hexane/ethyl acetate=5:1) to obtain a mixture of an optically active compound and a meso compound in a yield of about 40%. The mixture was purified by flash chromatography (silica gel, hexane/acetone=5:1) to obtain the optically active compound with an optical purity of 95% ee in a yield of about 30%. The resulting compound was recrystallized from ethyl acetate four times to finally obtain 490 mg of diphosphetane with an optical purity of 99% ee or more. The yield was 10%.

Physical Property Data
    $^1$H NMR (CDCl$_3$) δ1.30 (d, $^3J_{HP}$=17.0 Hz, 18H), 1.95-2.15 (m, 4H), 2.25-2.50 (m, 2H), 2.55-2.75 (m, 2H), 3.60-3.84 (m, 2H)
    $^{13}$C NMR δ19.53 (dd, 21.7 Hz, 18.0 Hz), 24.3 (s), 25.85 (dd, $J_{CP}$=47.2 Hz, 1.8 Hz), 35.41 (dd, $J_{CP}$=34.2 Hz, 2.5 Hz), 38.02 (dd, $J_{CP}$=44.7 Hz, $^2J_{CP}$=6.8 Hz)
    $^{31}$P NMR (1H decoupled, CDCl$_3$) δ90.29 (s)
    IR (KBr) 2970, 2947, 2364, 1460, 1366, 896, 808, 708, 646 cm$^{-1}$
    HRMS calculated value (C$_{14}$H$_{29}$P$_2$S$_2$ (M+H$^+$)) 323.1186, observed value 323.1198
    Elemental analysis calculated value (C$_{14}$H$_{28}$P$_2$S$_2$): C, 52.15; H, 8.75, observed value: C, 52.24; H, 8.80.
    $[\alpha]^{25}_D$ −160° (95% ee, c 0.99, CHCl$_3$)

Example 4

Synthesis of (1S,1S',2R,2R')-1,1'-diboranato-1,1'-di-tert-butyl-[2,2]'-diphosphetane The inside of a well-dried 300-mL two-necked flask was sufficiently replaced with argon, and 4.32 g (30 mmol) of 1-boranato-1-tert-butyl-phosphetane prepared in Example 2 was charged in the flask. To the flask, 8.44 g (36 mmol) of sparteine and then 70 mL of dry ether were added using a syringe, followed by stirring. After cooling to −78° C. in a dry ice/methanol bath, s-BuLi (36 mmol) was slowly added to the resultant mixture using a syringe. After the addition, the mixture was stirred at −78° C. for 3 hours, and 6.05 g (45 mmol) of copper chloride was added at a time. After the flask was returned to room temperature over 2 hours, the solution was further stirred at room temperature for 12 hours. After the stirring, 150 mL of 25% ammonia water was added to terminate reaction. Furthermore, 100 mL of ethyl acetate was added for a separation operation. An aqueous layer was subjected to three times of extraction with 100 mL of ethyl acetate each, and the collected organic layers were washed with 5% ammonia, 2M HCl, pure water, and brine, dehydrated over anhydrous sodium sulfate, and then concentrated. The concentrate was purified by flash chromatography (silica gel, hexane/ethyl acetate=20:1), and the obtained solute was recrystallized from hexane to obtain 650 mg of target (1S,1S',2R,2R')-1,1'-diboranato-1,1'-di-tert-butyl-[2,2']-diphosphetane. The yield was 15%. As a result of measurement of the optical purity of the target compound by chiral HPLC (Daicel OD-H, hexane:2-propanol=99:1, 0.5 mL/min, UV 210 nm), the optical purity was 100% ee.

Physical Property Data

Melting point: 147-149° C. (decomposition)

$^1$H NMR (CDCl$_3$) δ0.60 (br q, J$_{HB}$=106.0 Hz, 6H), 1.23 (d, 18H), 1.64-1.81 (m, 2H), 1.96-2.20 (m, 4H), 2.30-2.62 (m, 2H), 3.10-3.34 (m, 2H)

$^{13}$C NMR δ13.74 (d, J$_{CP}$=39.8 Hz), 22.84 (dd, $^2$J$_{CP}$=13.1 Hz, $^2$J$_{CP}$=15.5 Hz), 24.89 (d, $^3$J$_{CP}$=3.1 Hz), 29.64 (d, J$_{CP}$=16.8 Hz), 32.15 (d, J$_{CP}$=34.2 Hz)

$^{31}$P NMR (1H decoupled, CDCl$_3$) δ67.8-69.9 (m)

Example 5

Synthesis of (1S,1S',2R,2R')-1,1'-di-tert-butyl-[2,2']-diphosphetane

In a 100-mL two-necked flask, 129 mg (0.4 mmol) of (1R,1R',2R,2R')-1,1'-di-tert-butyl-[2,2']-diphosphetanyl 1,1'-disulfide was dissolved in 8 mL of degassed dry benzene under an argon stream. To the flask, 1.56 g (5.8 mmol) of hexachlorodisilane was added. The reaction solution was refluxed under heating for 3 hours and then cooled to 0° C. To the cooled flask, a 30% aqueous solution of sodium hydroxide was carefully added dropwise using a dropping funnel. After the dropping was completed, the mixture in the flask was heated to 50° C. under stirring until an aqueous layer became transparent. An organic layer was removed using a syringe, and the aqueous layer was subjected to two times of extraction with degassed hexane. The organic layers were collected and dehydrated over anhydrous sodium sulfate, and the solvent was distilled off to obtain a crude product. The thus-obtained crude product was purified by a basic alumina column to obtain 78 mg of (1S,1S',2R,2R')-1,1'-di-tert-butyl-[2,2']-diphosphetane. The yield was 75%. The resultant compound was easily-oxidizable and thus led directly to a rhodium complex.

Example 6

Synthesis of [rhodium(I)((1S,1S',2R,2R')-1,1'-di-tert-butyl-[2,2']-diphosphetane) (norbornadiene)]tetrafluoroborate In an argon stream, 78 mg (0.3 mmol) of (1S,1S',2R,2R')-1,1'-di-tert-butyl-[2,2']-diphosphetane prepared in the previous example was dissolved in 4 mL of THF. The resultant solution was added to a suspension cooled to 0° C. and containing 102 mg (0.27 mmol) of [rhodium(I)(dinorbornadiene)]tetrafluoroborate and 10 mL of THF. The reaction solution was stirred at room temperature for 3 hours. After the completion of reaction, an insoluble substance was filtered off using a cerite column under an argon stream. The filtrate was concentrated with an evaporator, and the purified orange solid was washed twice with 5 mL of diethyl ether and dried under reduced pressure. The resultant crude product was recrystallized from a small amount of THF to obtain 31 mg of the target rhodium catalyst. The yield was 20%.

Physical Property Data $^{31}$P NMR (1H decoupled, CDCl$_3$) δ114.90 (d, J$_{PRh}$=147 Hz)

Example 7

Synthesis of (1S,1S',2R,2R')-1,1'-di-tert-butyl-[2,2']-diphosphetane

In a 50-mL two-necked flask, 143 mg (0.5 mmol) of (1S,1S',2R,2R')-1,1'-diboranato-1,1'-di-tert-butyl-[2,2']-diphosphetane was dissolved in 3 mL of degassed dry dichloromethane under an argon stream, and the resultant solution was cooled to 0° C. To the flask, 0.68 mL (5 mmol) of a tetrafluoroboric acid-diethyl ether complex was added using a microsyringe. The reaction solution was stirred at room temperature for 12 hours and then cooled to 0° C. To the cooled flask, 12 mL of a 1 mol/L aqueous solution of sodium hydrogen carbonate solution was carefully added dropwise using a dropping funnel. After the dropping was completed, the resultant mixture was stirred for 2 hours, and degassed diethyl ether was added to extract an organic substance three times. The extracted organic layers were collected and dehydrated over anhydrous sodium sulfate, and the solvent was distilled off to obtain a crude product. The thus-obtained crude product was purified by a basic alumina column to obtain 107 mg of (1S,1S',2R,2R')-1,1'-di-tert-butyl-[2,2']-diphosphetane. The yield was 83%. The resultant compound was easily-oxidizable and thus led directly to a rhodium complex.

Example 8

Synthesis of (rhodium(I)((1S,1S',2R,2R')-1,1'-di-tert-butyl-[2,2']-diphosphetane)(norbornadiene)] hexafluorophosphate In an argon stream, 107 mg (0.41 mmol) of (1S, 1S', 2R, 2R')-1,1'-di-tert-butyl-[2,2']-diphosphetane prepared in Example 7 was dissolved in 2 mL of dichloromethane. The resultant solution was added to a suspension cooled to 0° C. and containing 160 mg (0.37 mmol) of [rhodium (I)(dinorbornadiene)]hexafluorophosphate and 5 mL of THF. The reaction solution was stirred at room temperature for 3 hours. After the completion of reaction, an insoluble substance was filtered off using a membrane filter under an argon stream. The filtrate was concentrated with an evaporator, and the produced orange solid was washed twice with 5 mL of diethyl ether and dried under reduced pressure to obtain the title compound.

Physical Property Data

Melting point: 130° C. (decomposition)

$^1$H NMR (CDCl$_3$) δ 1.23 (d, J$_{HB}$=12.2 Hz, 18H), 1.83 (m, 2H), 1.07 (m, 2H), 2.21 (m, 4H), 2.43 (m, 2H), 2.77 (m, 2H), 4.26 (s, 2H), 5.74 (d, J=25.1 Hz, 2H), 5.75 (d, J=4.6 Hz, 2H)

$^{31}$P NMR (1H decoupled, CDCl$_3$) δ 114.8 (d, J$_{P-Rh}$=148 Hz), 143.7 (h, J$_{P-F}$=711 Hz)

IR (KBr) 2940, 1465, 1310, 1180, 840, 560 cm$^{-1}$

Example 9

Asymmetric Reduction of Methyl α-acetamidocinnamate Using Rhodium Catalyst

In a 50-mL glass autoclave containing a magnetic stirrer, 219 mg (1 mmol) of methyl α-acetamidocinnamate used as a substrate and 1 mg (0.002 mmol) of [rhodium(I) ((1S,1S',2R, 2R')-1,1'-di-tert-butyl-[2,2']-diphosphetane)(norbornadiene)]tetrafluoroborate synthesized in Example 6 and used as a catalyst were charged. The inside of the reaction system was sufficiently replaced with hydrogen gas, and then a cock of the autoclave was partially opened to rapidly add 5 mL of methanol as a solvent and then closed. The autoclave was cooled by immersion in a dry ice/ethanol bath, and the reaction system was evacuated, followed by vacuum breaking with hydrogen gas (2 atm). This operation was repeated four times, and then the bath was removed. The reaction system was stirred at room temperature for 3 hours until the hydrogen pressure was no more decreased. After the completion of reaction, vacuum breaking was carefully performed with hydrogen gas, and the resultant reaction solution was analyzed directly with chiral HPLC (Daicel OD-H, hexane:2-propanol=9:1). As a result of the analysis, a reductant with an optical purity of 96.8% ee was obtained in a reaction yield of 99% or more.

<Asymmetric Hydrogenation Reaction of Dehydroamino Acid Derivative and Enamide Derivative>

Examples 10 to 22

In a 50-mL autoclave, 6 mg (1.0×10$^{-2}$ mmol) of the [rhodium(I)((1S,1S',2R,2R')-1,1'-do-tert-butyl-[2,2']-diphosphetane)(norbornadiene)]hexafluorophosphate synthesized in Example 8 and used as a catalyst and 1 mmol of the dehydroamino acid derivative (or enamide derivative) shown in Table 1 were charged. Then, the system was evacuated and purged with hydrogen four times. The autoclave was returned to normal pressure, and a cock was opened to rapidly add 4 mL of degassed dehydrated methanol from the cock using a syringe and then closed. The reactor was cooled with dry ice/ethanol, and then the reaction system was again evacuated and purged with hydrogen four times. After the hydrogen pressure was set to a predetermined value, the refrigerant was removed, and the reaction system was stirred with a magnetic stirrer until hydrogen consumption was stopped. After the completion of reaction, the reaction solution was passed through silica gel column chromatography (developing solvent: ethyl acetate) to remove the catalyst, and then the residue was concentrated with an evaporator to obtain a reduced product. In any reaction, the yield was about 100%. The optical purity (ee) of each product was analyzed with chiral HPLC or chiral GC. The results are shown in Table 1. These results were obtained at a ratio of substrate:catalyst=100:1.

TABLE 1

Asymmetric hydrogenation reaction of dehydroamino acid derivative and enamide derivative using [rhodium(I) ((1S,1S',2R,2R')-1,1'-do-tert-butyl-[2,2']-diphosphetane) (norbornadiene)]hexafluorophosphate (cat.) as a catalyst

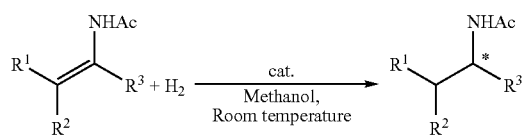

| Example | R$^1$ | R$^2$ | R$^3$ | Hydrogen pressure (atm) | Reaction time (h) | ee (%) (Conf.)$^{b,c}$ |
|---|---|---|---|---|---|---|
| 10 | Ph | H | CO$_2$Me | 1 | 1 | >99(R) |
| 11 | Ar$^a$ | H | CO$_2$Me | 1 | 1 | >99(R) |
| 12 | H | H | CO$_2$Me | 1 | 1 | >99(R) |
| 13 | Me | Me | CO$_2$Me | 6 | 5 | 15(R) |
| 14 | —(CH$_2$)$_4$— | | CO$_2$Me | 6 | 5 | 1(R) |
| 15 | H | H | Ph | 1 | 1 | >99(R) |
| 16 | H | H | 4-MeOC$_6$H$_4$ | 1 | 1 | 99(R) |
| 17 | H | H | 4-O$_2$NC$_6$H$_4$ | 1 | 11 | >99(R) |
| 18 | Me | H | Ph | 1 | 1 | >99(R) |
| 19 | H | Me | Ph | 2 | 1 | 37(R) |
| 20 | Me | Me | Ph | 3 | 12 | 70(R) |
| 21 | H | H | t-C$_4$H$_9$ | 1 | 1 | 93(S) |
| 22 | H | H | 1-adamantyl | 1 | 1 | 62(S) |

In the table,
$^a$Ar represents 3-methoxy-4-acetyloxyphenyl group
$^b$Conf. represents the absolute configuration at an asymmetric point of a product.
$^c$Determined by chiral GC or chiral HPLC.

Example 23

Catalytic Activity Test of [rhodium(I)((1S,1S',2R, 2R')-1,1'-di-tert-butyl-[2,2']-diphosphetane)(norbornadiene)]hexafluorophosphate Using Asymmetric Hydrogenation Reaction of Methyl α-acetamidocinnamate:substrate:catalyst=50,000:1

In a 10-mL two-necked egg-shaped flask containing a magnetic stirrer, 2 mg (3.3 μmol) of the [rhodium (I) ((1S,1S',2R, 2R')-1,1'-di-tert-butyl-[2,2']-diphosphetane)(norbornadiene)]hexafluorophosphate prepared in Example 8 was precisely weighed and charged. The inside of the flask was replaced with argon, and then 2 mL of degassed and dehydrated methanol was precisely measured with a syringe and added to the flask. The resultant mixture was stirred until the solution became completely homogenous. Next, a magnetic stirrer and 779 mg (3.3 mmol) of methyl α-acetamidocinnamate used as a substrate were placed in a 50-mL autoclave. Then, 40 μL of a methanol solution (concentration 1.66 μmol/mL) of the catalyst prepared as described above was precisely measured with a microsyringe and added to the autoclave. The autoclave contained 3.3 mmol of the substrate and 6.7× 10$^{-2}$ pmol of the catalyst, and thus the ratio of substrate: catalyst was 50000:1. Next, the inside of the autoclave was replaced with argon, and 4 mL of degassed and dehydrated methanol was rapidly added to the autoclave. Then, the autoclave was sealed and cooled by immersion in a dry ice/ethanol bath, and the reaction system was evacuated, followed by vacuum breaking with hydrogen gas. This operation was repeated four times, and then the internal pressure of the autoclave was increased to 6 atm. The bath was removed, and the reaction system was stirred at room temperature until the hydrogen pressure was no more decreased. As a result, reduction of the gage pressure was stopped after stirring for 43 hours, and thus the termination of the reaction was confirmed. After the reaction was terminated, vacuum breaking was carefully performed with hydrogen gas, and the reaction solution was passed through silica gel column chromatography (developing solvent: ethyl acetate) to remove the catalyst and then concentrated with an evaporator to obtain a reduced product. The yield was about 100%. The optical purity (ee) of the product was analyzed with chiral HPLC (Daicel OD-H, hexane:2-propanol=9:1). As a result of the analysis, the optical purity of the reductant was 99% or more.

INDUSTRIAL APPLICABILITY

According to the present invention, an optically active phosphorus heterocyclic dimer can be obtained, and a transition metal complex containing the dimer as a ligand is useful as an asymmetric hydrogenation catalyst.

The invention claimed is:

1. A process for producing a phosphorus heterocyclic dimer according to formula (5) comprising the steps of:

reacting, in the presence of a n-butyl lithium, primary phosphine represented by formula (1):

R—PH$_2$      (1)

(wherein R represents a linear or a branched alkyl group having 2 to 20 carbon atoms or a cyclic alkyl group having 3 to 20 carbon atoms) with a compound represented by formula (2):

Y—C$_n$H$_{2n-Y}$      (2)

(wherein Y represents a halogen atom or a leaving group selected from -OTs, -OTf, and -OMs, and n represents a number of 3 to 6);

reacting a product, which was obtained by said step of reacting primary phosphine represented by formula (1) with a compound represented by formula (2), with boron trihydride, oxygen, or sulfur to obtain a phosphorus heterocyclic compound represented by formula (3):

(wherein R represents a linear or a branched alkyl group having 2 to 20 carbon atoms or a cyclic alkyl group having 3 to 20 carbon atoms, n equals 1, X represents a boron trihydride group, an oxygen atom, or a sulfur atom, and ═══ represents a single bond when X is a boron trihydride group or a double bond when X is an oxygen atom or sulfur atom);

dimerizing the phosphorus heterocyclic compound represented by formula (3) to produce a phosphorus heterocyclic dimer represented by formula (4):

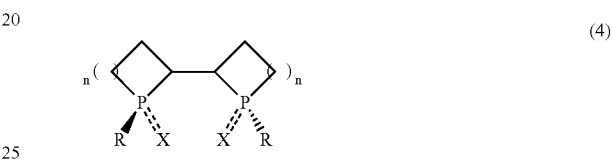

(wherein R represents a linear or a branched alkyl group having 2 to 20 carbon atoms or a cyclic alkyl group having 3 to 20 carbon atoms, n equals 1, X represents a boron trihydride group, an oxygen atom, or a sulfur atom); and removing oxygen, sulfur, or borane from the phosphorus heterocyclic dimer represented by formula (4) to obtain an optically active phosphorus heterocyclic dimer represented by formula (5):

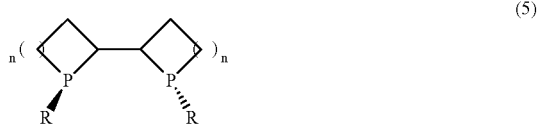

wherein R represents a linear or a branched alkyl group having 2 to 20 carbon atoms or a cyclic alkyl group having 3 to 20 carbon atoms, n equals 1); and wherein the compound represented by formula (2) is 1,3-dichloropropane.

* * * * *

UNITED STATES PATENT AND TRADEMARK OFFICE
CERTIFICATE OF CORRECTION

| | |
|---|---|
| PATENT NO. | : 7,411,096 B2 |
| APPLICATION NO. | : 10/564985 |
| DATED | : August 12, 2008 |
| INVENTOR(S) | : Nobuhiko Oohara et al. |

It is certified that error appears in the above-identified patent and that said Letters Patent is hereby corrected as shown below:

<u>Column 23</u> in claim 1, line 40 "$Y-C_nH_{2n\,-Y}$" should read -- $Y-C_nH_{2n}-Y$ --

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,411,096 B2 Page 1 of 1
APPLICATION NO. : 10/564985
DATED : August 12, 2008
INVENTOR(S) : Nobuhiko Oohara et al.

It is certified that error appears in the above-identified patent and that said Letters Patent is hereby corrected as shown below:

On title page, Item (57), ABSTRACT in line 7, "Y–$C_nH_{2n-Y}$" should read -- Y–$C_nH_{2n}$–Y --

Signed and Sealed this

Twenty-fifth Day of November, 2008

JON W. DUDAS
*Director of the United States Patent and Trademark Office*